(12) United States Patent
Mercier et al.

(10) Patent No.: US 6,511,486 B2
(45) Date of Patent: Jan. 28, 2003

(54) DERMABRASION HAND TOOL FOR ABRASIVELY REMOVING SKIN SURFACE

(75) Inventors: Charles Mercier, Montréal (CA); Marc Hoffman, Montréal (CA)

(73) Assignee: Silhouet-Tone Ltee, Laval (CA)

( * ) Notice: Subject to any disclaimer, the term of this patent is extended or adjusted under 35 U.S.C. 154(b) by 0 days.

(21) Appl. No.: 09/803,512

(22) Filed: Mar. 9, 2001

(65) Prior Publication Data

US 2002/0128663 A1 Sep. 12, 2002

(51) Int. Cl.[7] ............................... A61M 1/00
(52) U.S. Cl. .................. 606/131; 604/289; 604/313
(58) Field of Search ........................... 606/131, 132, 606/159; 604/289, 290, 313, 315

(56) References Cited

U.S. PATENT DOCUMENTS

| | | | |
|---|---|---|---|
| 2,608,032 A | 8/1952 | Garver | 51/11 |
| 2,921,585 A | 1/1960 | Schumann | 128/355 |
| 3,085,573 A | 4/1963 | Meyer et al. | 128/240 |
| 3,574,239 A | 4/1971 | Sollerud | 4/1 |
| 3,715,838 A | 2/1973 | Yong et al. | 51/12 |
| 4,540,365 A * | 9/1985 | Nelson et al. | 433/88 |
| 4,560,373 A | 12/1985 | Sugino et al. | 604/30 |
| 4,646,480 A | 3/1987 | Williams | 51/424 |
| 4,676,749 A | 6/1987 | Mabille | 433/88 |
| 4,757,814 A | 7/1988 | Wang et al. | 128/318 |
| 5,037,432 A | 8/1991 | Molinari | 606/131 |
| 6,039,745 A * | 3/2000 | Di Fiore et al. | 606/131 |
| 6,235,039 B1 * | 5/2001 | Parkin et al. | 606/131 |
| 6,277,128 B1 * | 8/2001 | Muldner | 606/133 |

* cited by examiner

Primary Examiner—John J. Wilson
Assistant Examiner—Michael B. Priddy
(74) Attorney, Agent, or Firm—Darby & Darby

(57) ABSTRACT

A dermabrasion hand tool for abrasively removing a skin surface by means of an abrasive stream projected onto the skin surface to be removed. The hand tool includes an elongated manipulative body having a longitudinal axis and first and second opposite ends. The hand tool also includes an operative head through which the abrasive stream is projected onto the skin surface to be removed and through which the removed skin surface and used abrasive stream are evacuated, the operative head being removably mounted onto the first end of the manipulative body. The hand tool further includes a supply channel for supplying,the abrasive stream to the operative head from a supply stream source, and an evacuating channel for evacuating the removed skin surface and used abrasive stream from the operative head to an evacuating means, both of said channels extending within and along the manipulative body and each having first and second extremities located respectively at the first and second ends of the manipulative body. The hand tool is characterized in that its operative head has a projection head for projecting the abrasive stream orthogonally to the skin surface to be removed; an evacuation chamber operatively connected to the evacuating channel for facilitating evacuation of the removed skin surface and used abrasive stream into the evacuating channel; and rotation-inducing mechanisms for giving a rotational pattern to the abrasive stream projected from the operative head.

16 Claims, 17 Drawing Sheets

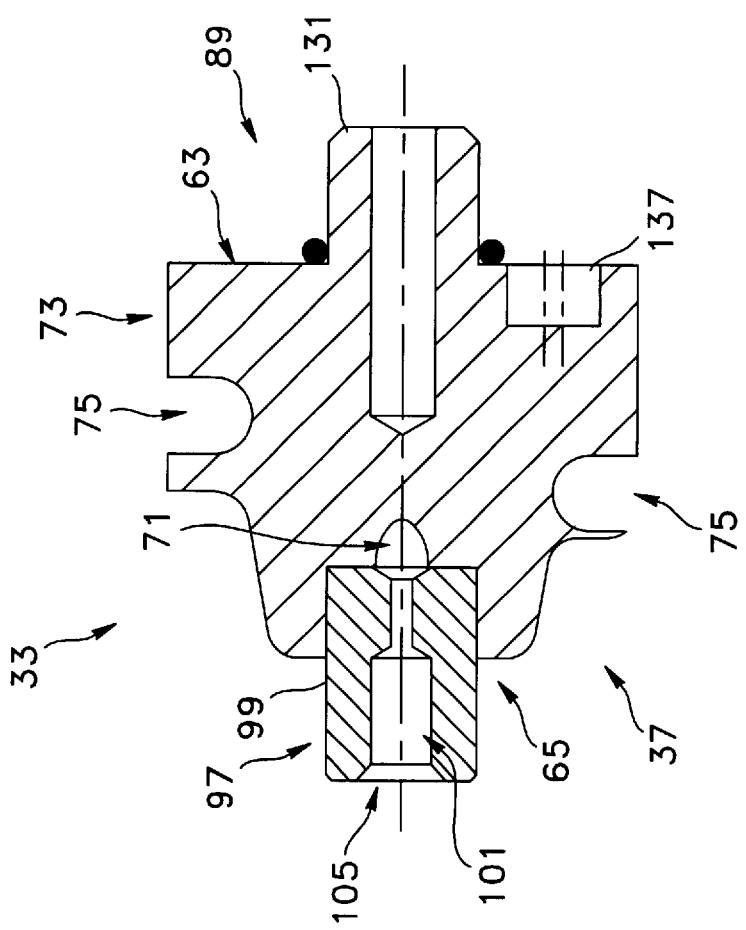
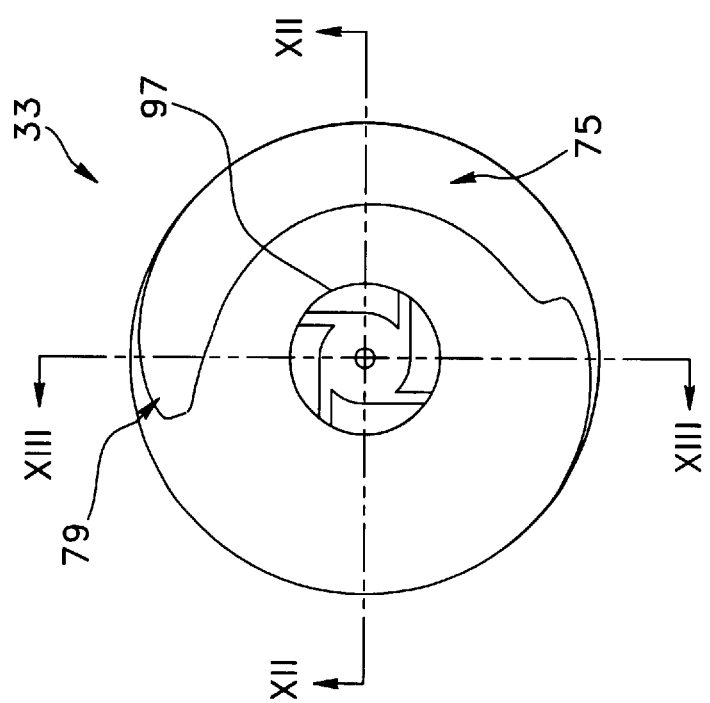
FIG. 13
FIG. 11

DERMABRASION HAND TOOL FOR ABRASIVELY REMOVING SKIN SURFACE

FIELD OF THE INVENTION

The present invention relates to a hand tool hereinafter called "dermabrasion hand tool" for abrasively removing skin surface. More particularly, the present invention relates to a dermabrasion hand tool devised so as to allow a controlled and stable removal of superficial skin surface by the projection of a fine abrasive stream onto the skin surface to be removed, said fine abrasive stream being projected and retrieved in a rotational pattern and orthogonally to and from the skin surface to be removed.

BACKGROUND OF THE INVENTION

Devices used for aesthetic applications in the field of skin treatment are well known in the art. These devices generally consist of hand tools used for abrasively removing layers of human skin in such a way as to ultimately obtain aesthetic improvements of the skin being treated. Depending on the application and the desired end result, such superficial skin abrasion may range from a light abrasion where the outermost layers of the epidermis are removed, to a much deeper abrasion where the dermis is involved. Therefore, it would be useful to provide a hand tool which enables a controlled and adjustable removal of superficial skin surface by the projection of an abrasive stream onto the skin surface to be removed.

An example of the hand tools known in the art is disclosed in U.S. Pat. No. 5,037,432 granted on Aug. $6^{th}$, 1991 to Molinari. This patent describes an apparatus which is used to remove surface portions of human tissues in an adjustable manner and essentially comprises a tool provided with a supply tube along which abrasive reducing substances are conveyed under pressure. A throughhole in the head disposed along the axis of the tube permits the substances to abrade the region of tissue facing the hole. A collection tube in which Is created a depression is provided for the purpose of removing under suction both the reducing substances and the portions of tissue removed during the treatment.

A major problem associated with the above-mentioned device is that the hand tool is devised to project the abrasive stream onto the skin surface to be removed at a tilted angle, which gives rise to an abrasion pattern on the skin surface in the form of a "half-moon". This is undesirable because, as it is known in the art, axisymmetrical abrasion patterns, such as a circular pattern for example, enable for a much more uniform and thus improved superficial skin abrasion, leading ultimately to better aesthetic skin improvements. Another problem associated with the above-mentioned type of hand tool is that the latter is generally devised to be operated at an optimal tilted angle with respect to the skin surface being worked upon, said tilted angle being generally very difficult for a manual operator of the device to keep constantly with respect to the surface being worked upon throughout the entire duration of the treatment. This leads to fluctuations in time of the abrasion patterns on the skin surface being worked upon which is also undesirable for obvious reasons known in the art. Therefore, it would be useful to provide a hand tool which would enable a more even skin abrasion pattern than what is possible with the devices known in the prior art, both in surface geometry and in time.

Also known in the art are hand tools which are devised to project the abrasive stream orthogonally to the skin surface to be removed. These devices are generally more practical than the above-discussed hand tools, since they are designed to be operated orthogonally to the skin surface worked upon, thereby simplifying positioning and handling thereof. However, a major problem associated with these types of devices is that instead of adequately removing layers of skin, because they project the abrasive stream orthogonally to the skin surface to be removed, they tend to mark said skin surface being worked upon with deep cavities, a phenomenon commonly known as "pitting" or "skin stabbing" which is also undesirable for obvious reasons known in the art. Therefore, it would be useful to provide a hand tool which enables to project an abrasive stream orthogonally to the skin surface to be removed without causing "skin stabbing" thereon.

It is also known in the art that most of the hand tools used for abrasively removing layers of skin tend to be of elaborate construction, thereby making them quite difficult to assemble, use and/or maintain. Therefore, it would be useful to provide a hand tool which is easy to assemble, easy to use, and easy to maintain.

Also known to the Applicant are the following US patents which describe other devices used for clinical applications or abrasive purposes: U.S. Pat. Nos. 2,608,032; 2,921,585; 3,085,573; 3,574,239; 3,715,838; 4,560,373; 4,646,480; 4,676,749; and 4,757,814.

None of the above-mentioned patents seems to disclose or even suggest a dermabrasion hand tool which can project and retrieve an abrasive stream to and from the skin surface to be removed in a rotational pattern and orthogonally thereto, Furthermore, none of the above-mentioned patents seems to disclose or even suggest a dermabrasion hand tool which enables a controlled and adjustable removal of superficial skin surface by the projection of an abrasive stream onto the skin surface to be removed, while providing a substantially even skin abrasion pattern, both in surface geometry and in time. Moreover, none of the above-mentioned patents seems to disclose or even suggest a dermabrasion hand tool which is easy to assemble, easy to use, and easy to maintain.

SUMMARY OF THE INVENTION

The main objects of the present invention are to provide a dermabrasion hand tool which satisfies each of the above-mentioned needs.

More particularly, a first object of the invention is to provide a dermabrasion hand tool which enables a controlled and adjustable removal of superficial skin surface by the projection of an abrasive stream onto the skin surface to be removed.

A second object of the invention is to provide a dermabrasion hand tool which enables a more even skin abrasion pattern than what is possible with the devices known in the prior art, both in surface geometry and in time.

A third object of the invention is to provide a dermabrasion hand tool which enables to project and retrieve the abrasive stream to and from the skin surface to be removed in a rotational pattern and orthogonally thereto.

A fourth object of the invention is to provide a dermabrasion hand tool which is easy to assemble, easy to use, and easy to maintain.

In accordance with the invention, the above objects are achieved by a dermabrasion hand tool for abrasively removing a skin surface by means of an abrasive stream projected onto the skin surface to be removed, the abrasive stream after projection onto said skin surface becoming a used abrasive stream, said hand tool comprising:

an elongated manipulative body having a longitudinal axis and first and second opposite ends;

an operative head through which the abrasive stream is projected onto the skin surface to be removed and through which the removed skin surface and used abrasive stream are evacuated, said operative head being removably mounted onto the first end of the manipulative body; and a supply channel for supplying the abrasive stream to the operative head from a supply stream source, and an evacuating channel for evacuating the removed skin surface and used abrasive stream from the operative head to an evacuating means, both of said channels extending within and along the manipulative body and each having first and second extremities located respectively at the first and second ends of the manipulative body;

wherein the operative head comprises:
a projection head for projecting the abrasive stream orthogonally to the skin surface to be removed;
an evacuation chamber operatively connected to the evacuating channel for facilitating evacuation of the removed skin surface and used abrasive stream into said evacuating channel; and
rotation-inducing means for giving a rotational pattern to the abrasive stream projected from the operative head.

The invention and its advantages will be better understood by reading the following non-restrictive description of a preferred embodiment thereof, made with reference to the accompanying drawings.

BRIEF DESCRIPTION OF THE DRAWINGS

FIG. 11 is a top plan view of the projection head shown in FIG. 3.

FIG. 13 is a cross-sectional view taken along section XIII—XIII of the projection head shown in FIG. 11.

DETAILED DESCRIPTION OF A PREFERRED EMBODIMENT OF THE INVENTION

Figure 1:
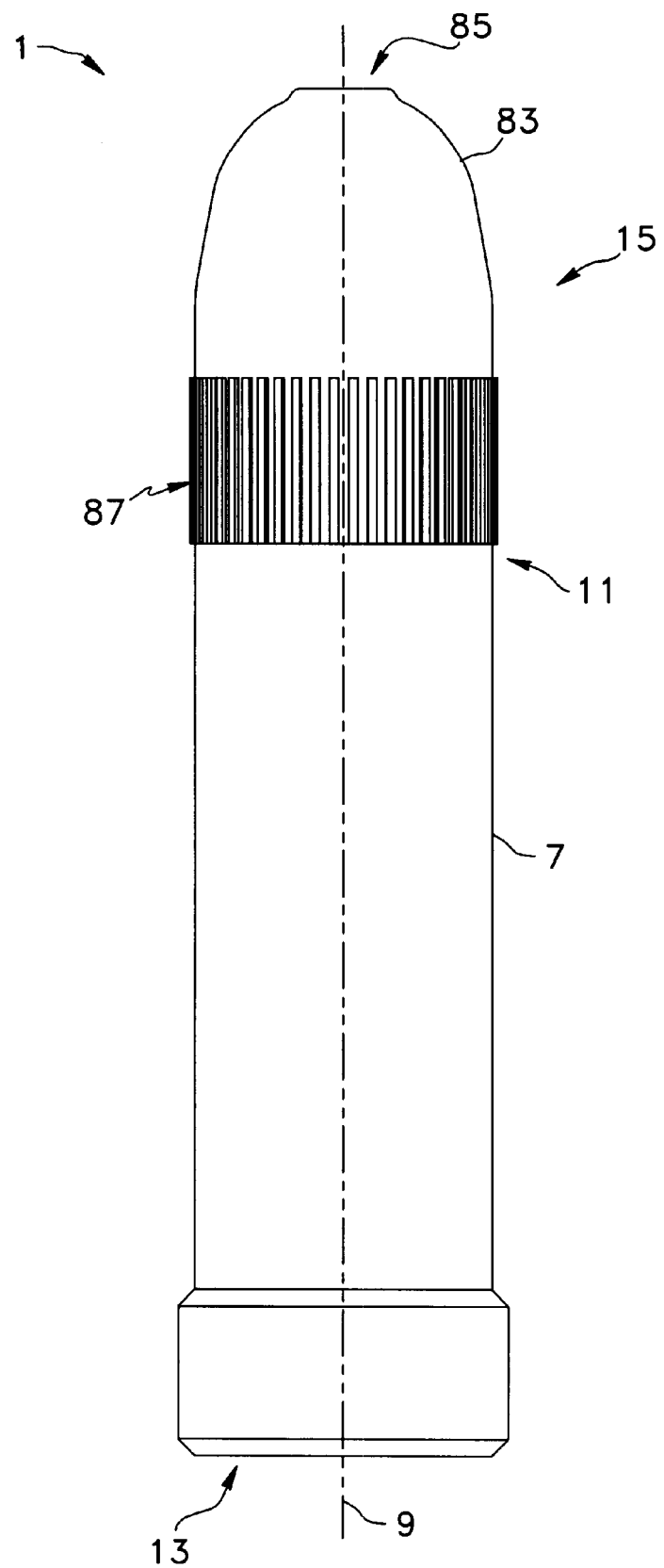
FIG. 1 is a plan view of the dermabrasion hand tool according to a preferred embodiment of the invention.

In the following description, the same numerical references refer to similar elements.

Moreover, although the present invention was primarily intended for aesthetic and clinical applications in the field of human skin treatment, it could be used for other applications with other objects of different fields, as apparent to a person skilled in the art. For this reason, expressions such as "human", "skin", and/or "abrasive stream" and any other references and/or other expressions equivalent thereto should not be taken as to limit the scope of the present invention and include all other objects with which the present application could be used. As apparent to a person skilled in the art, the present invention may be used for other projection applications, such as surface painting purposes for example, where the "abrasive stream" would be "paint particles".

In addition, the expressions "stream" and "powder", as well as any equivalent expressions and/or compound words thereof, may be used interchangeably in the context of the present description. The same applies for expressions such as "skin" and "surface", "removed" and "exfoliated", and for any other mutually equivalent expressions, as apparent to a person skilled in the art.

The dermabrasion hand tool 1 according to the preferred embodiment of the invention shown in the accompanying drawings, FIGS. 1 to 21, is a dermabrasion hand tool 1, used in conjunction with a dermabrasion system 2, for abrasively removing a skin surface 3 by means of an abrasive stream 5 projected onto the skin surface 3 to he removed. The abrasive stream 5 after projection onto the skin surface 3 becomes a "used" abrasive stream 5. The hand tool 1 comprises an elongated manipulative body 7 having a longitudinal axis 9 and first and second opposite ends 11, 13. The hand tool 1 also comprises an operative head 15 through which the abrasive stream 5 is projected onto the skin surface 3 to be removed and through which the removed skin surface 3 and used abrasive stream 5 are evacuated, The operative head 15 is preferably removably mounted onto the first end 11 of the manipulative body 7. The hand tool 1 also comprises a supply channel 17 for supplying the abrasive stream 5 to the operative head 15 from a supply stream source 19, and an evacuating channel 21 for evacuating the removed skin surface 3 and used abrasive stream 5 from the operative head 15 to an evacuating means 23. Both channels 17, 21 preferably extend within and along the manipulative body 7 and each has first and second extremities 25, 27, 29, 31 located respectively at the first and second ends 11, 13 of the manipulative body 7. The hand tool 1 is characterized in that the operative head 15 comprises a projection head 33 for projecting the abrasive stream 5 orthogonally to the skin surface 3 to be removed, an evacuation chamber 35 operatively connected to the evacuating channel 21 for facilitating evacuation of the removed skin surface 3 and used abrasive stream 5 into the evacuating channel 21, and rotation-inducing means 37 for giving a rotational pattern to the abrasive stream 5 projected from the operative head 15. These rotation-inducing means 37 are devised preferably also to enable retrieval of the removed skin surface 3 and used abrasive stream 5 in a rotational pattern from the skin surface 3 being treated, as will be explained in greater detail hereinbelow.

Figure 4:
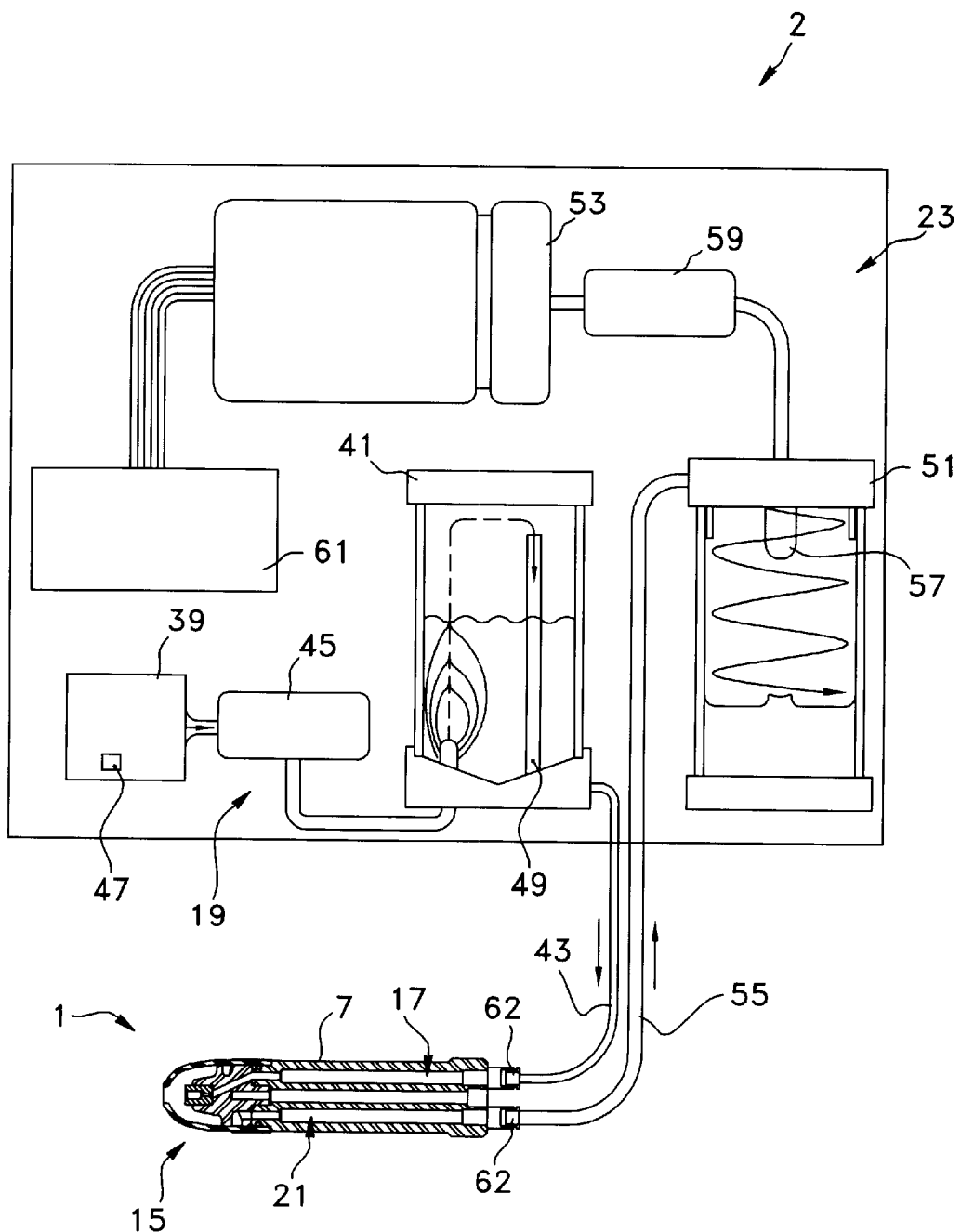
FIG. 4 is a schematic view of the hand tool shown in FIG. 1 being used with a dermabrasion system according to a preferred embodiment of the invention.
Figure 5:
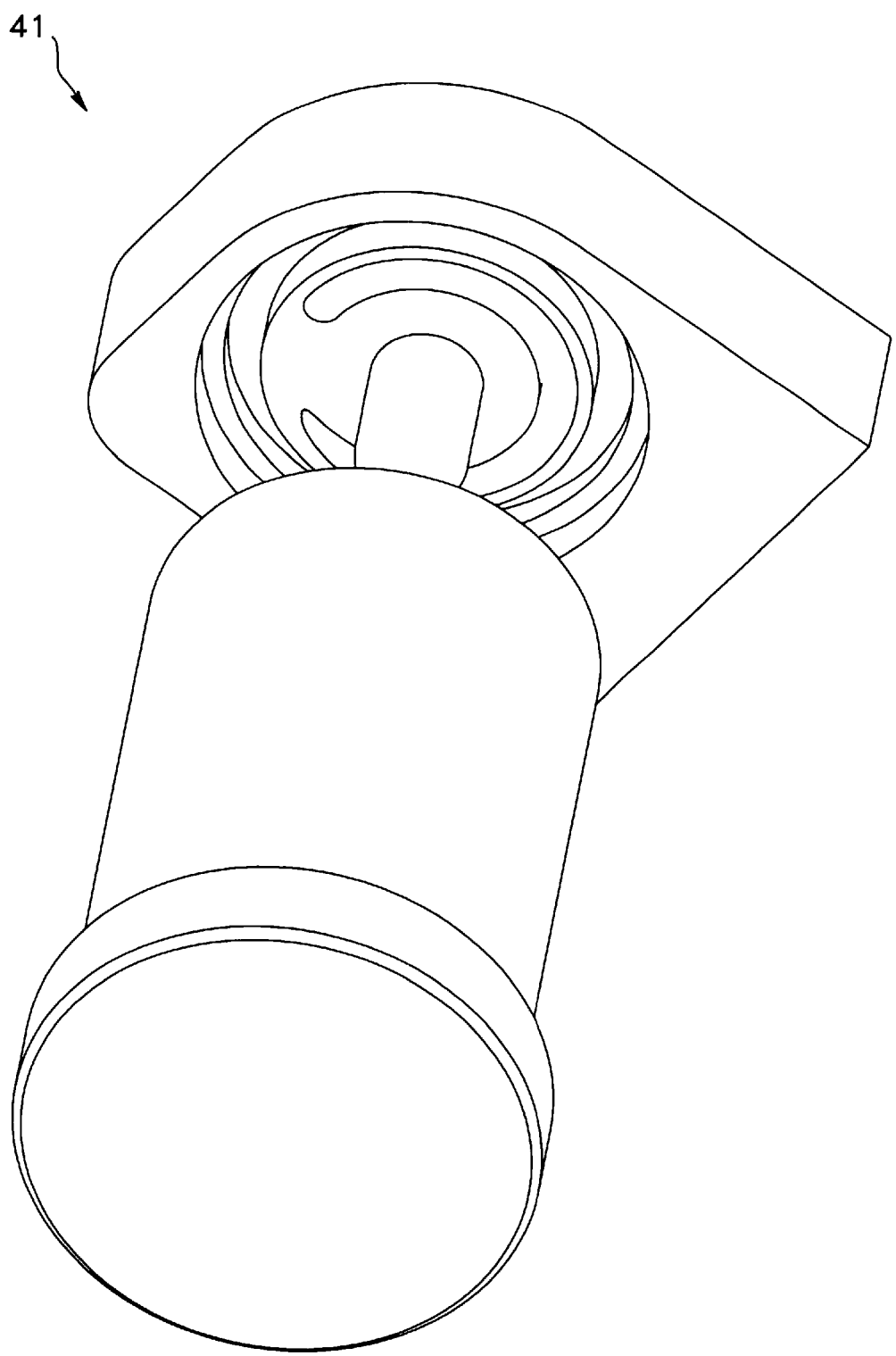
FIG. 5 is an exploded view of the components of the main filter assembly shown in FIG. 4.

As better shown in FIG. 4, the supply stream source 19 preferably comprises a compressor 39 which maintains under pressure air contained within a "fresh" powder reservoir 41 filled with clean abrasive powder, the reservoir 41 being operatively connected to the supply channel 17 of the hand tool 1 preferably by means of a flexible tube 43. The compressor 39 is preferably devised for appropriately generating compressed air so as to be able to convey clean abrasive powder under pressure from the fresh powder reservoir 41 to and along the supply channel 17 of the hand tool 1, in order to provide the projection head 33 of the hand tool 1 with a clean abrasive stream 5. It is worth mentioning that an auxiliary filter 45 may be connected between the compressor 39 and the fresh powder reservoir 41 so as to filter out unwanted impurities coming from the compressor 39. Preferably, the compressor 39 comprises a regulator 47 so as to be able to control and adjust the output parameters of the compressed air. Preferably also, the fresh powder reservoir 41 also comprises a regulator 49 to be used for controlling and adjusting the output parameters of the clean abrasive stream 5.

As also shown in FIG. 4, the evacuating means 23 preferably comprise a "used" powder reservoir 51 and a vacuum pump 53. It is to be understood that the expression "used powder" here designates both the removed skin surface 3 and the used abrasive stream 5, as well as any other normal operating impurities of the system. Preferably, the vacuum pump 53 is operatively connected, via the evacuating channel 21 and the other components shown, such as a flexible tube 55 for example, to the evacuating chamber 35 of the hand tool 1 for creating therein a depression, so as to remove under suction both the removed skin surface 3 and used abrasive stream 5 into the evacuating channel 21, and ultimately into the used powder reservoir 51. The used powder reservoir 51 is preferably provided with a filter 57 so as to filter out the impurities, i.e. removed skin surface 3, used abrasive stream 5, etc., from the air being sucked into the vacuum pump 53. It is worth noting that an auxiliary filter 59 may be connected between the used powder reservoir 51 and the vacuum pump 53 so as to further filter out undesirable impurities. Moreover, the vacuum pump 53 preferably comprises a regulator 61 so as to control the intensity of the suction effect. The above-mentioned components and their regulators 47, 49, 61, as well as the design of the present invention, as will be further explained hereinbelow, enable an operator of the hand tool 1 to carry out abrasions of different extents and depths of portions of human skin surface 3, thereby allowing a controlled and adjustable skin abrasion.

It is worth mentioning that other components and/or interconnections thereinbetween may be used respectively for the supply stream source 19 and evacuating means 23 of the hand tool 1, as apparent to a person skilled in the art, without departing from the scope of the present invention. For example, the second extremities 29, 31 of the supply and evacuating channels 17, 21 are preferably provided with push-in connectors 62, as better shown in FIG. 2, so as to facilitate connection of the flexible tubes 43, 55 to their corresponding channels 17, 21. Furthermore, as can be easily understood, adequate substances with appropriate dimensions (grain size, etc.) are used for the abrasive powder (abrasive stream 5), as apparent to a person skilled in the art, depending on the applications for which the hand tool 1 is intended. Moreover, as also apparent to a person skilled in the art, appropriate materials are selected for the various components of the hand tool 1, explained in greater detail hereinbelow, given the notable abrasion that the abrasive stream 5 may exert on the internal surfaces of these components. Indeed, materials such as aluminum are to be avoided, for reasons well known in the art, because this material may contaminate the abrasive stream 5 being projected to the skin surface 3 and in turn contaminate the blood of the patients being treated. Therefore, appropriate materials which will not contaminate the abrasive stream 5, such as polymers and/or stainless steels, should be used, as apparent to a person skilled in the art. Preferably also, the abrasive stream 5 being projected is a homogeneous stream 5.

Figure 2:
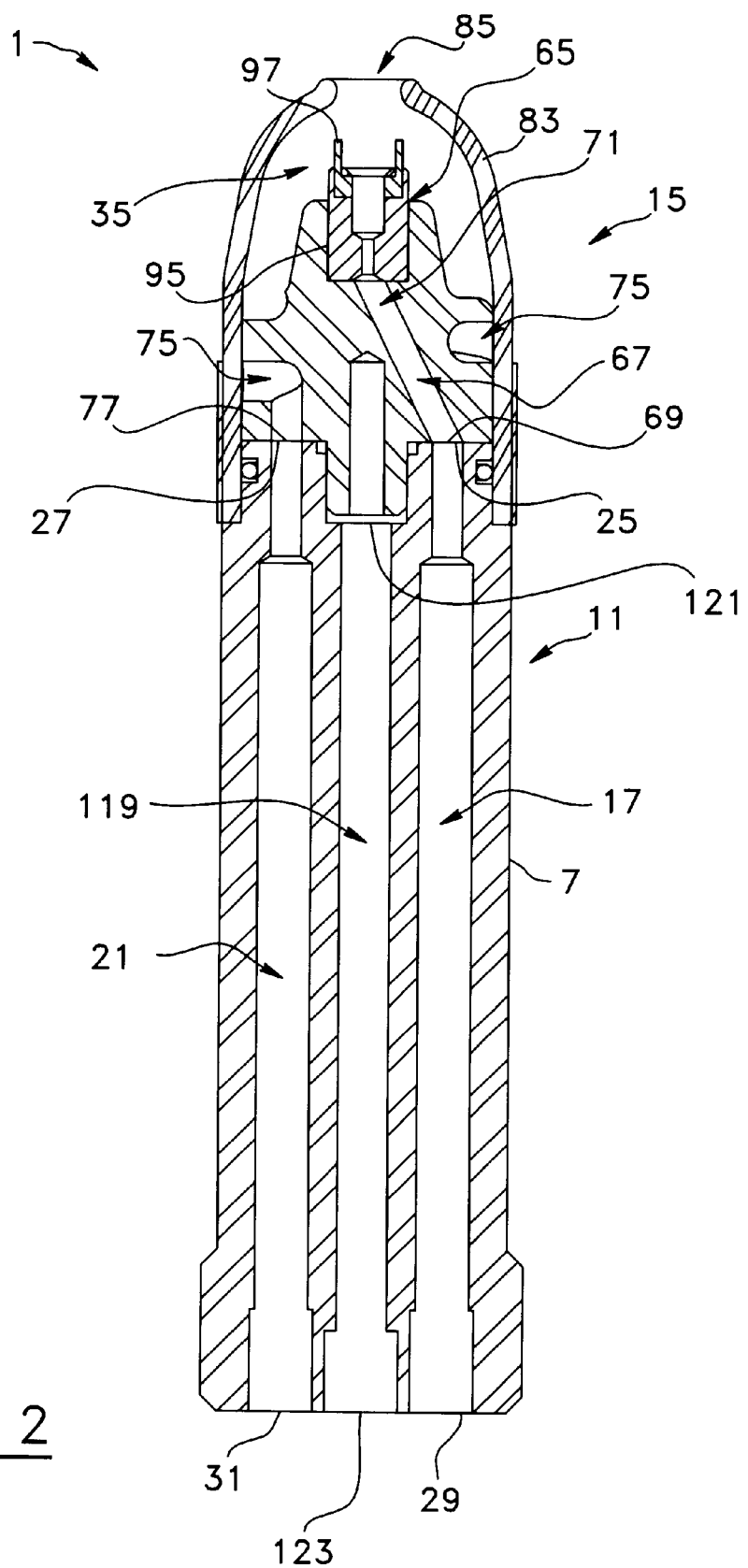
FIG. 2 is a schematic cross-sectional view taken along the longitudinal axis of the hand tool shown in FIG. 1.
Figure 3:
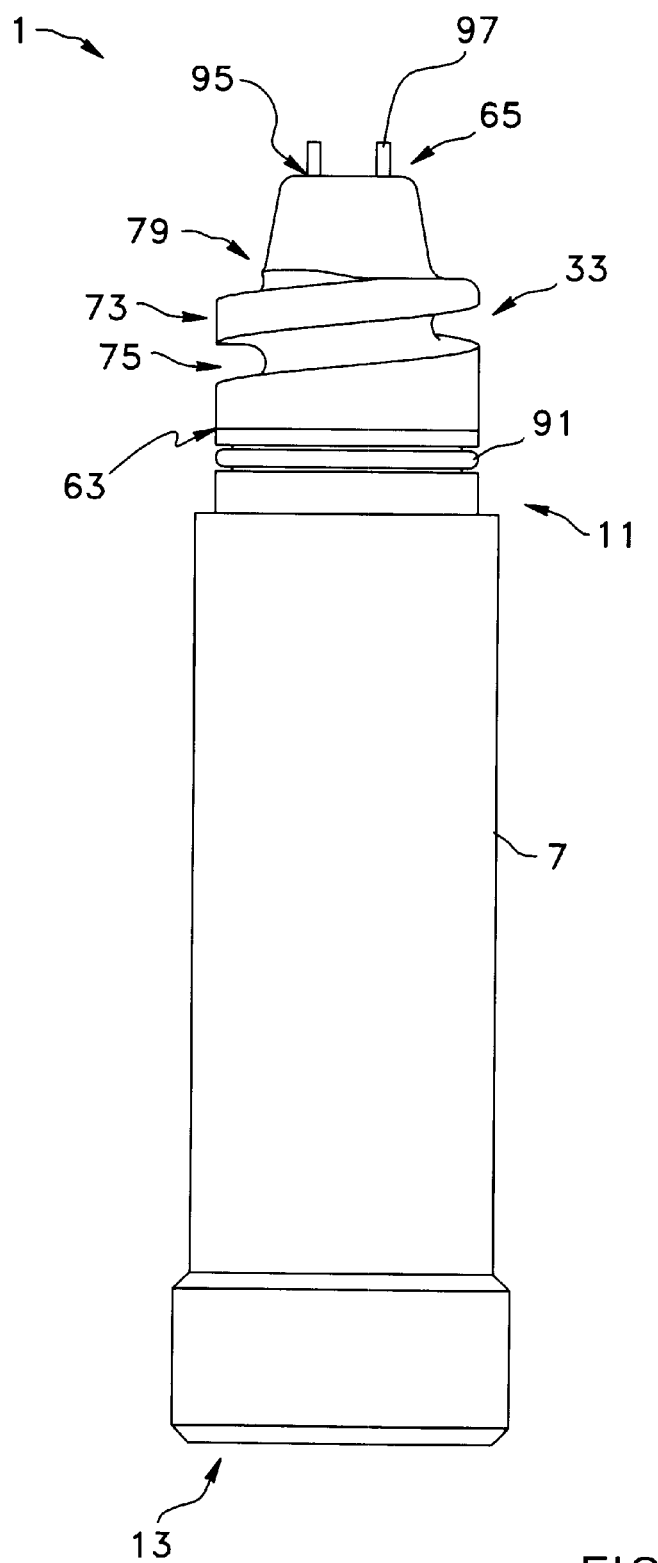
FIG. 3 is a plan view of the hand tool shown in FIG. 1, said hand tool being shown with no cap.

As better shown in FIGS. 2 and 3, the projection head 33 preferably comprises a base 63 removably mounted to the first end 11 of the manipulative body 7, a tip 65 opposite to the base 63 and through which the abrasive stream 5 is projected, and a feeding channel 67 extending inside the projection head 33 from the base 63 to the tip 65 thereof. The feeding channel 67 preferably has a first extremity 69 connected to the first extremity 25 of the supply channel 17 and a second extremity 71 located adjacent to the tip 65 of the projection head 33 through which the abrasive stream 5 is projected. As can be easily understood, the clean abrasive stream 5 is provided from the fresh powder reservoir 41 to the tip 65 of the projection head 33 via the feeding channel 67 which is operatively connected to the supply channel 17.

As better shown in FIGS. 11 to 14, the projection head 33 preferably further comprises a peripheral outer surface 73 about a portion of which a spiral-shaped groove 75 extends coaxially. The spiral-shaped groove 75 preferably has a first extremity 77 connected to the first extremity 27 of the evacuating channel 21 and a second extremity 79 located on the peripheral outer surface 73 of the projection head 33 between the base 63 and the tip 65 thereof. The spiral-shaped groove 75 cooperates with the evacuation chamber 35 and is used, among other things, to evacuate the removed skin surface 3 and used abrasive stream 5 from the evacuation chamber 35 into the evacuating channel 21. As can be easily understood, the removed skin surface 3 and used abrasive stream 5 are evacuated, under the suction effect of the vacuum pump 53, through the operative head 15, as will be explained hereinbelow, from the evacuation chamber 35 of the operative head 15 to the used powder stream reservoir 51 via the spiral-shaped groove 75 which is operatively connected to the evacuating channel 21

It is worth mentioning here that, according to another embodiment of the present invention, more than one spiral-shaped groove 75 could extend about portions of the peripheral outer surface 73 of the projection head 33, such as a "manifold", each of which would have a first extremity 77 operatively connected to the evacuating channel 21 and a second extremity 79 located at an appropriate location on the peripheral outer surface 73 of the projection head 33. Furthermore, the first and second extremities 77, 79 of each spiral-shaped groove 75 may be respectively common to one another or not, depending on the applications of the hand tool 1. Moreover, the shape, size, and orientation of each spiral-shaped groove 75 are selected depending on the particular applications of the hand tool 1, as apparent to a person skilled in the art.

As better shown in FIGS. 7 to 10, the first end 11 of the manipulative body 7 preferably comprises a rim 81 onto which a cap 83 is removably mounted Preferably also, the cap 83 encases the projection head 33 forming thus the evacuating chamber 35 around the projection head 33 so as to facilitate evacuation of the removed skin surface 3 and used abrasive stream 5 via the spiral-shaped groove 75. The cap 83 preferably comprises a throughhole 85 through which the abrasive stream 5 is projected onto the skin surface 3 to be removed and through which the removed skin surface 3 and used abrasive stream 5 are sucked back into the evacuating chamber 35 so as to be evacuated via the spiral-shaped groove 75 through the evacuating channel 21, as better shown in FIGS. 2, 6, and 17. The throughhole 85 preferably consists of a circular orifice, although other suitable shapes may be used The throughhole 85 and the tip 65 of the projection head 33 are preferably aligned with the longitudinal central axis 9 of the manipulative body 7 so that the abrasive stream 5 is projected axially with respect to the hand tool 1 and thus orthogonally to the skin surface 3 to be removed when the hand tool 1 is positioned perpendicularly thereon. In use, the cap 83 is preferably laid perpendicularly over the skin surface 3 to be treated in such a way that the throughhole 85 faces directly the specific region of skin surface 3 to be removed. The abrasive stream 5 is projected from the projection head 33 through the throughhole 85 under the thrust of the air provided from the stream supply source 19, thereby causing removal of the skin surface 3 in the amount desired by the operator of the hand tool 1, as selected by controlling and adjusting the different regulators of the dermabrasion system 2. As can be easily understood, pressing the cap 83 against the skin surface 3 being treated so as to "seal" the working area allows the suction effect exerted in the evacuation chamber 35 by the vacuum pump 53.

Figure 6:
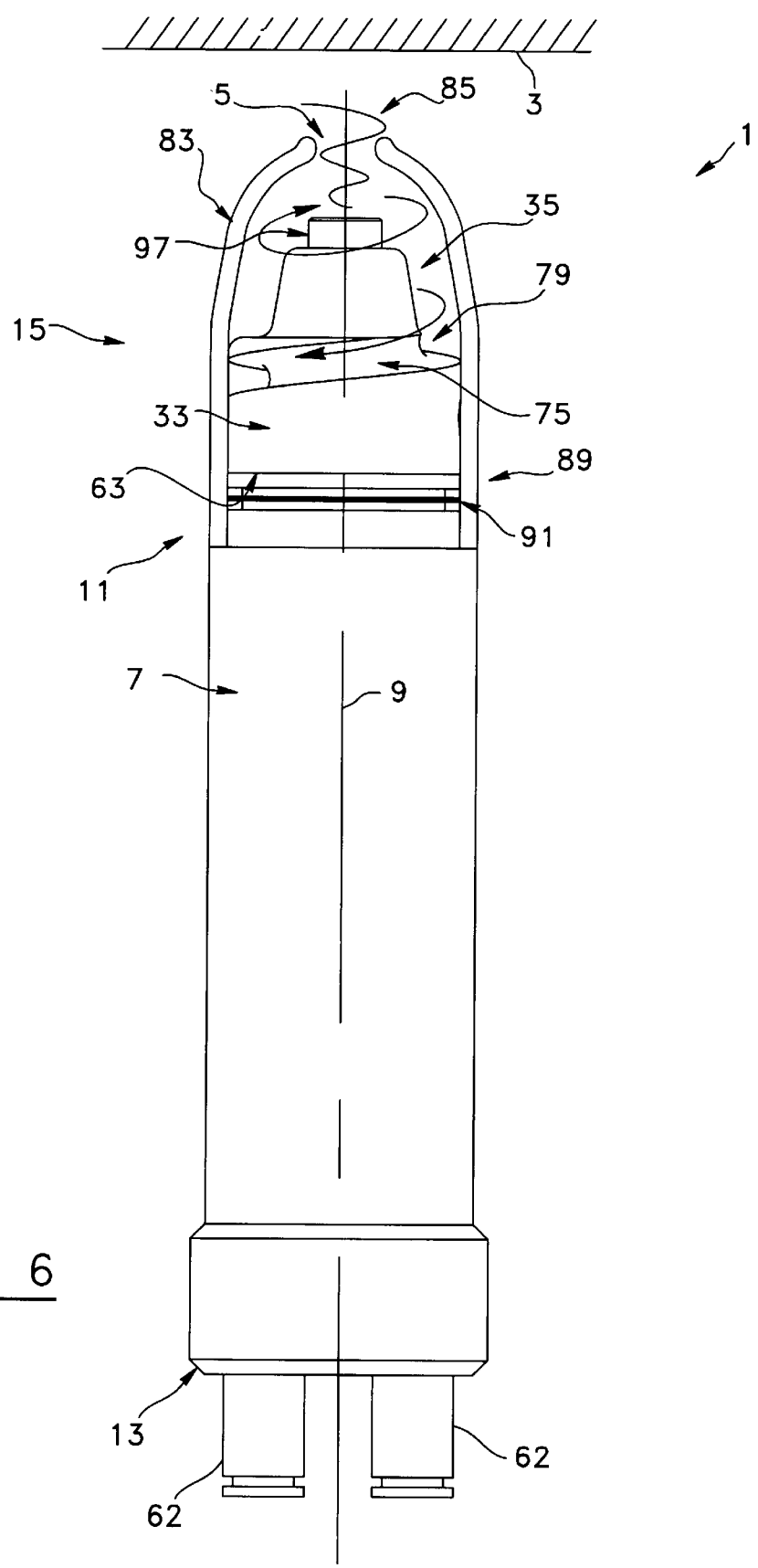
FIG. 6 is a plan view of the hand tool shown in FIG. 1, said hand tool being shown with a cross-sectional view of the cap taken along the longitudinal axis thereof.

Preferably, the cap 83 is made of a transparent material to allow a user of the hand tool 1 to see the abrasive stream 5 being projected and the removed skin surface 3 and used abrasive stream 5 being evacuated Preferably also, as shown in FIGS. 1, 2, and 6, the cap 83 has a substantially "bell-shaped" configuration, although other suitable shapes may be used. Preferably also, the cap 83 is made of an inexpensive material so as to be disposable after treating a particular patient with the hand tool 1. Preferably also, the cap 83 is provided with a knurled surface 87 along the bottom periphery thereof so as to facilitate gripping of the cap 83 and thus facilitating mounting/removal of the cap 83 onto the manipulative body 7. It is worth mentioning here that the shape and dimensions of the cap 83, as well as the distances thereof with respect to the projection head 33, are selected so as to ensure an effectively appropriate suction action exerted by the vacuum pump 53 in the evacuation chamber 35, as apparent to a person skilled in the art. The rim 81 of the manipulative body 7 is preferably provided with sealing means 89 so as to ensure an appropriate seal between the manipulative body 7 and the cap 83 mounted thereon Preferably also, the sealing means 89 consist of an o-ring gasket 91 and the gasket 91 is preferably housed within an annular groove 93 extending all around the rim 81 of the manipulative body 7. As apparent to a person skilled in the art, other suitable sealing means 89 appropriately cooperating with the cap 83 and manipulative body 7 may be used.

As better shown in FIGS. 11 to 14, the tip 65 of the projection head 33 preferably comprises a slot 95 projecting inwardly into the tip 65 of the projection head 33. The slot 95 is preferably devised to allow a projection nozzle 97 to be removably inserted into the tip 65 so as to adjust (i.e. affect) the flow of the abrasive stream 5 projected through the tip 65 of the projection head 33. It is worth mentioning here that other suitable means may be provided at the tip 65 of the projection head 33 so as to affect the flow of the abrasive stream 5 passing therethrough, as apparent to a person skilled in the art.

The projection nozzle 97 preferably consists of a hollow member comprising an outer surface 99 and an inner cylindrical projection channel 101, also known as a "nozzle cavity". Preferably also, the protection channel 101 comprises a first extremity 103 connected to the second extremity 71 of the feeding channel 67 and a second extremity 105 through which the abrasive stream 5 is projected. As can be easily understood, the clean abrasive stream 5 is provided to the second extremity 105 of the projection channel 101 from the fresh powder reservoir 41 via the projection channel 101, feeding channel 67, and supply channel 17, which are all operatively connected to one another.

Figure 16:
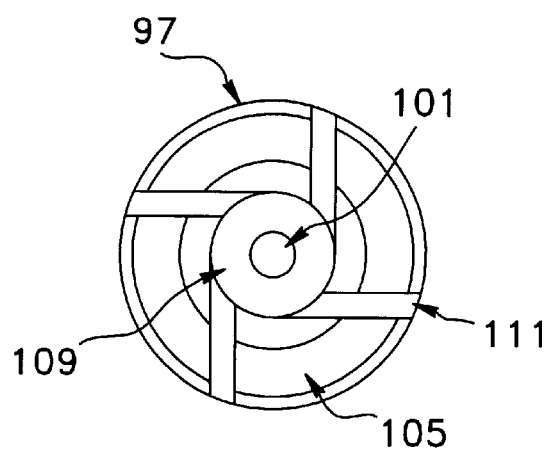
FIG. 16 is a top plan view of the projection nozzle shown in FIG. 14.
Figure 15:
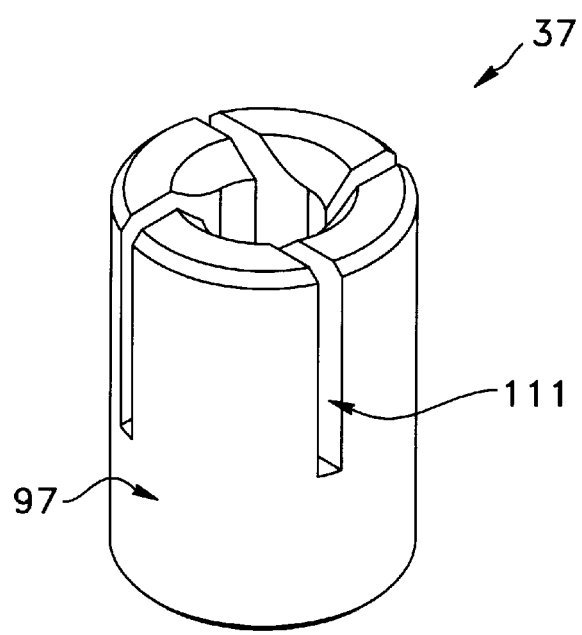
FIG. 15 is a perspective view of the projection nozzle shown in FIG. 12.
Figure 17:
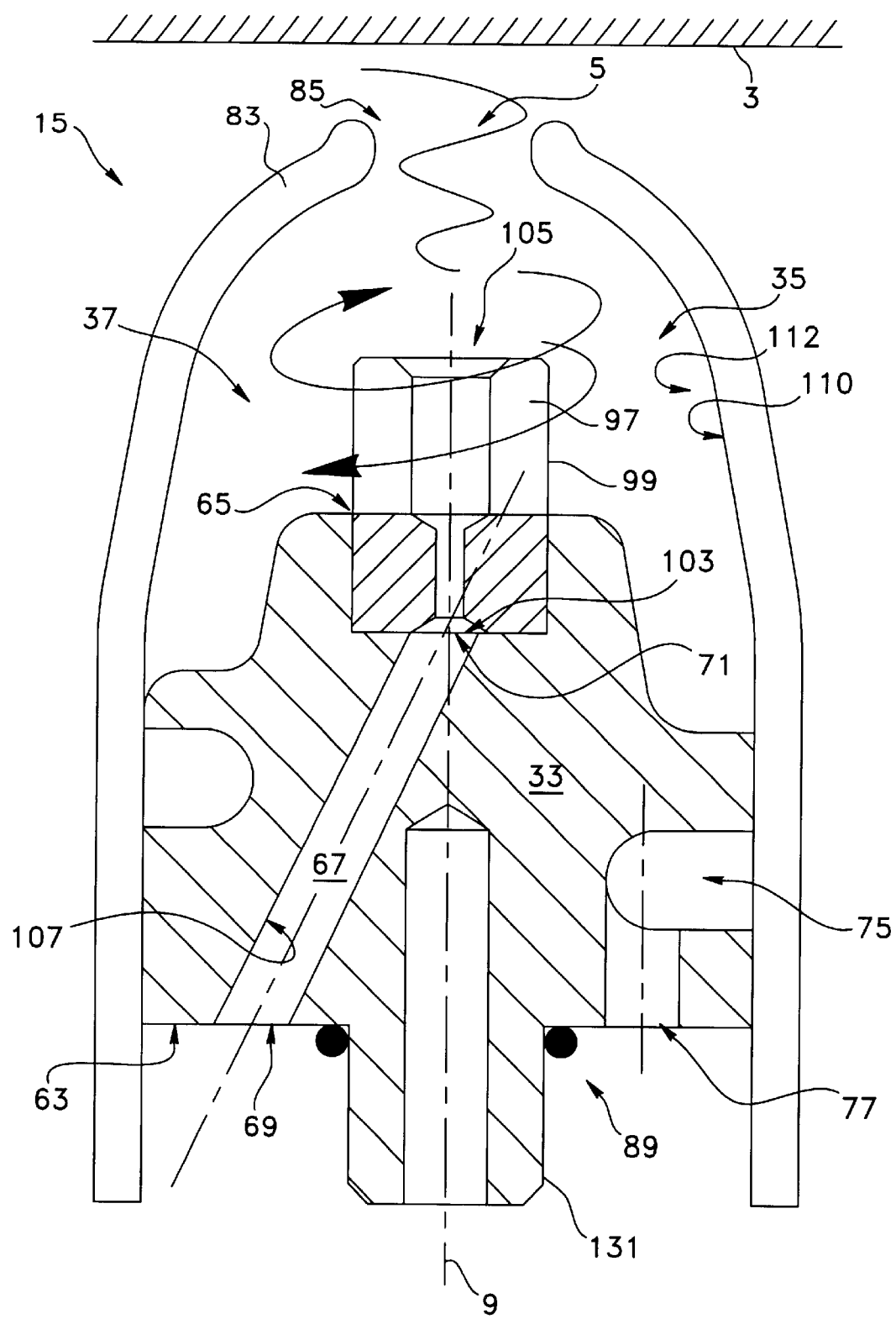
FIG. 17 is a sectional view of the operative head of the hand tool shown in FIG. 1.
Figure 18:
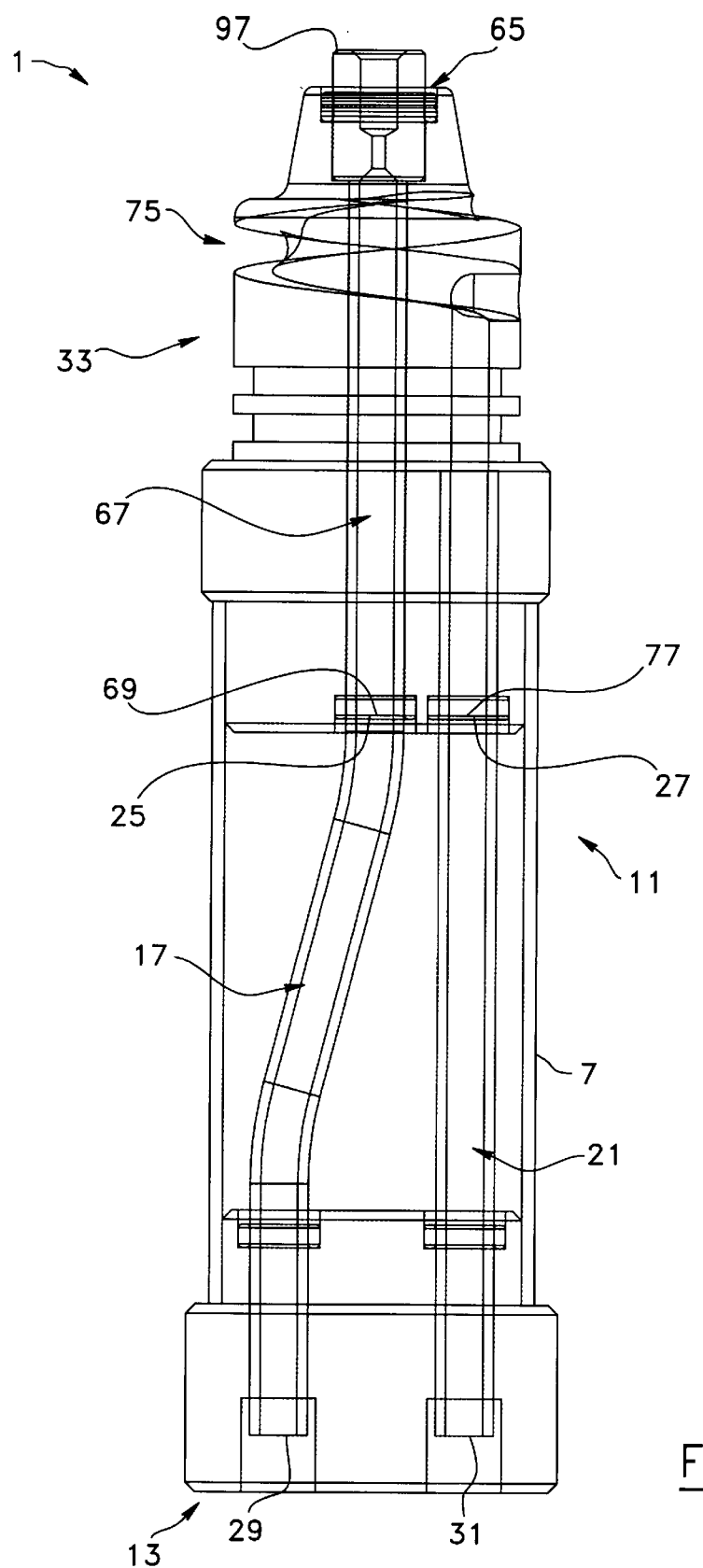
FIG. 18 is a front plan view of the dermabrasion hand tool according to another preferred embodiment of the invention, said hand tool being shown with no cap.
Figure 19:
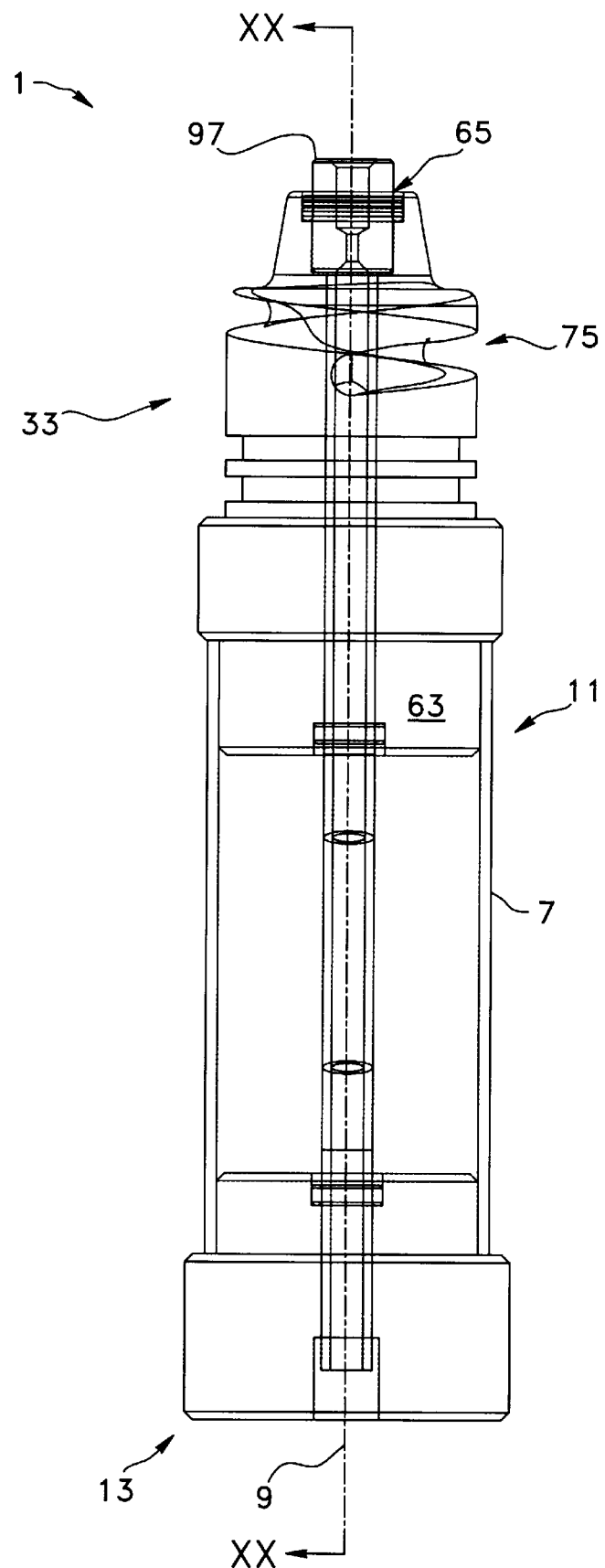
FIG. 19 is a side view of the hand tool shown in FIG. 18.
Figure 20:
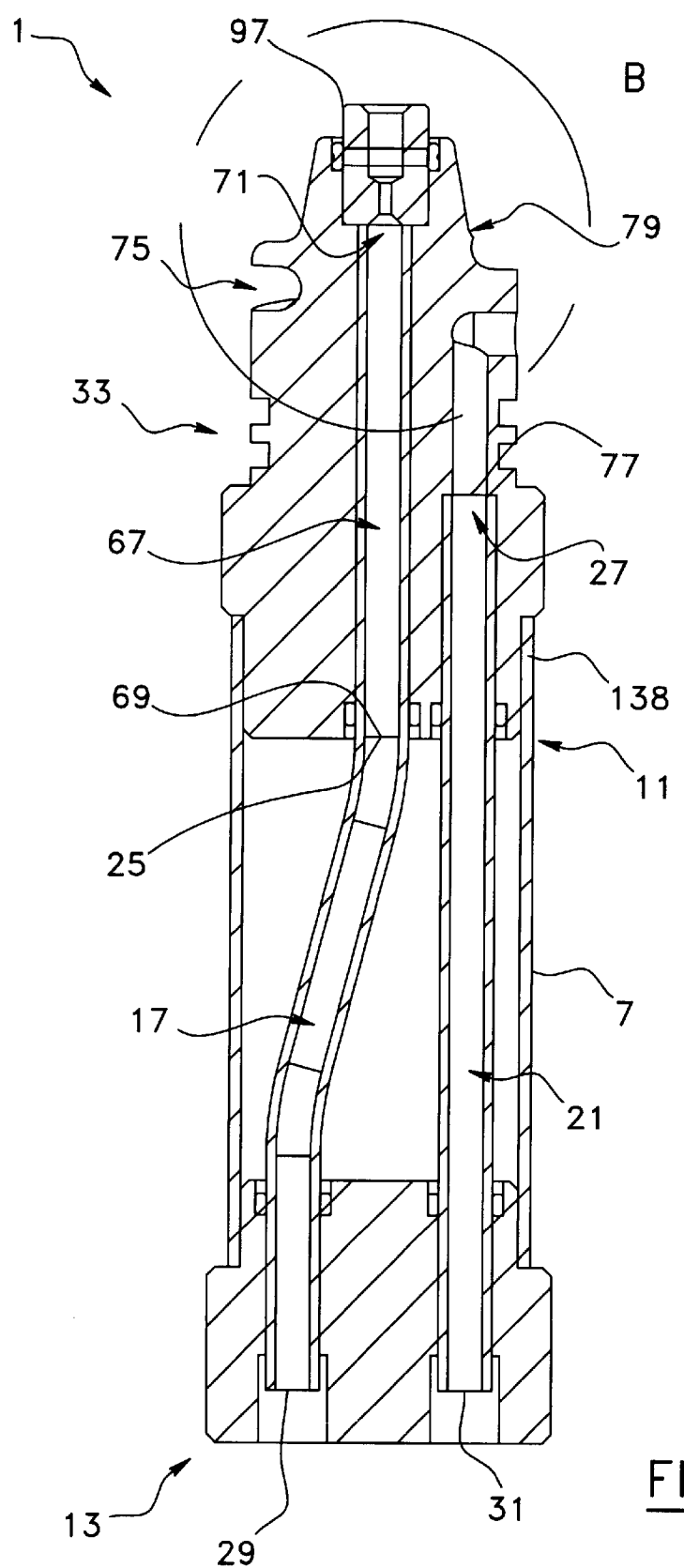
FIG. 20 is a cross-sectional view taken along section XX—XX of the hand tool shown in FIG. 19.
Figure 21:
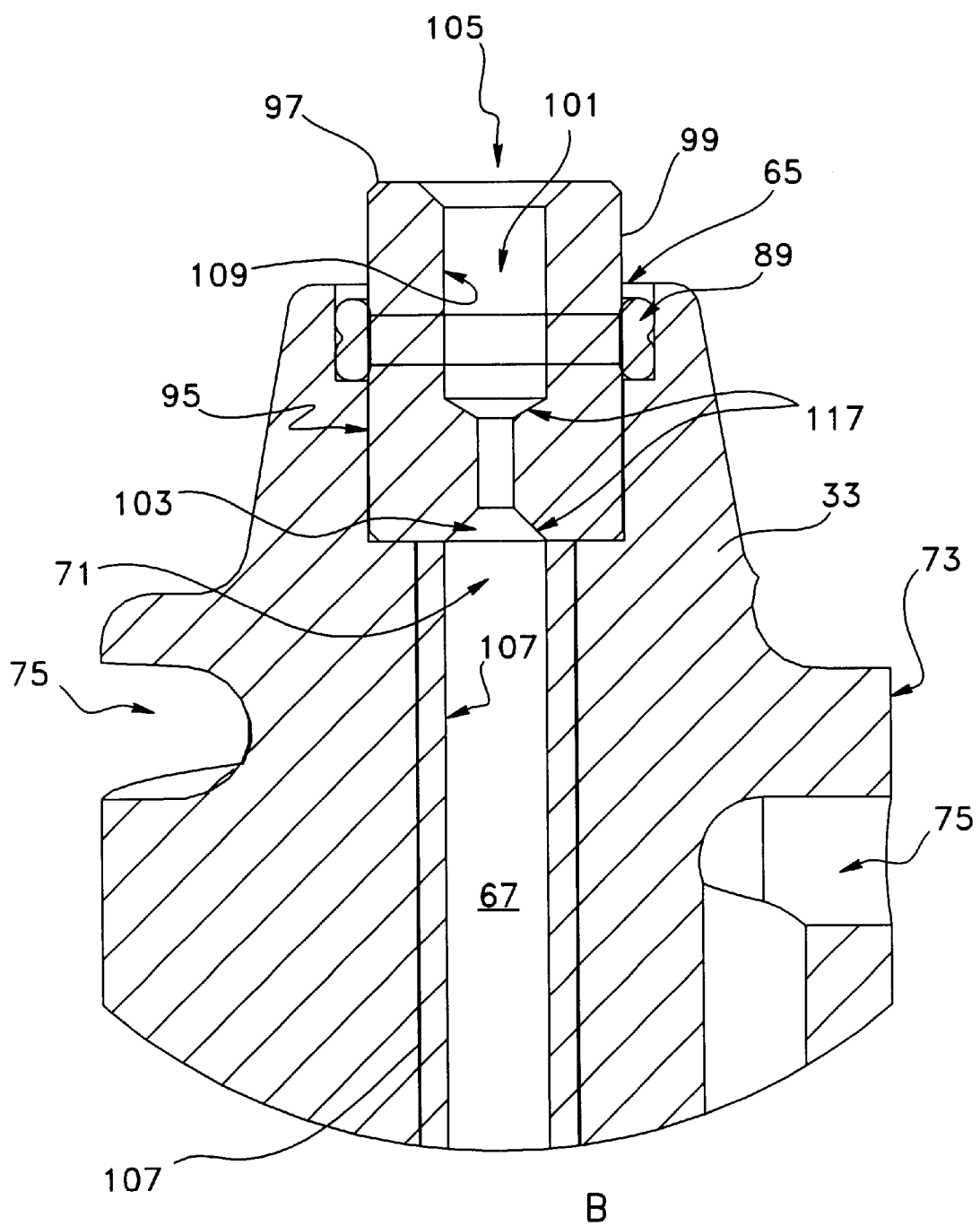
FIG. 21 is an enlarged view of section B of the projection head shown in FIG. 20.

According to the preferred embodiment of the invention and as better shown in FIGS. 15 to 17, the rotation-inducing means 37 of the hand tool 1 may include at least one coaxial groove 107 provided along the feeding channel 67 of the projection head 33 so as to induce the rotational pattern onto the abrasive stream 5 projected through the feeding channel 67. Preferably also, the rotation-inducing means 37 of the hand tool 1 further comprise at least one coaxial groove 109 provided along the projection channel 101 of the projection nozzle 97 so as to further induce the rotational pattern to the abrasive stream 5 projected through the projection channel 101. Moreover, the rotation-inducing means 37 of the hand tool 1 preferably comprise also at least one lateral slit 111 provided on the projection nozzle 97, each slit 111 extending preferably from the projection channel 101 to the outer surface 99 of the projection nozzle 97 and cooperating with the evacuation chamber 35 so as to further induce the rotational pattern to the abrasive stream 5 projected through the projection nozzle 97, as apparent to a person skilled in the art. Furthermore, the rotation-inducing means 37 may also comprise at least one coaxial groove 110 provided along an internal surface 112 of the cap 83 so as to induce an additional rotational pattern to the removed skin surface 3 and used abrasive stream 5 being evacuated from the evacuation chamber 35 into the evacuating channel 21 via the spiral-shaped groove 75. The above-mentioned rotation-inducing means 37 are intended, among other things, to provide the abrasive stream 5 with a spiral movement about the longitudinal axis 9 of the hand tool 1.

The at least one coaxial groove 109 provided along the projection channel 101 of the projection nozzle 97 preferably consists of an appropriate number of turbine-like fan blades suitably arranged along the projection channel 101 about the center axis thereof. Furthermore, the projection nozzle 97 is preferably provided with an appropriate number of spaced and oriented nozzle lateral slits 111, each being operatively connected to the evacuation chamber 35 and devised to permit a radially outward induced flow within the projection channel 101, and thus directly induce a rotational movement of the abrasive stream 5 circulating through projection channel 101 located within the projection nozzle 97. Such an obtained rotational flow is preferably transmitted to the abrasive stream 5 as it exits the projection channel 101 of the nozzle 97. This substantially radial and rotational movement of the abrasive stream 5 as induced by the above-described rotation-inducing means 37 allows the flow of the abrasive stream 5 to clear the evacuation chamber 35 more efficiently, significantly contributing to stabilizing the flow of the abrasive stream 5 because of its rotational component, leading thus to a more controlled abrasion, under various operating conditions of the components of the dermabrasion system 2 and under various operating angles of the hand tool 1 with respect to the normal plane (i.e. angles with respect to gravity)

As previously hinted, another component of the present invention used as part of the rotation-inducing means 37 is the spiral-shaped groove 75 of the projection head 33. Preferably, the spiral-shaped groove 75 by means of its design cooperating with the suction effect in the evacuation chamber 35, as explained hereinabove, induces an additional rotation to the abrasive stream 5 projected from the nozzle 97 before the abrasive stream 5 strikes the skin surface 3 at the throughhole 85 of the operative head 15. Preferably also, after the abrasive stream 5 has provided the required abrasion on the skin surface 3, the spiral-shaped groove 75 provides a rapid and unobtrusive removal of the abrasive stream 5 from the throughhole 85 and away from the longitudinal central area within the cap 83, by means of the rotation induced centrifugal forces, created by the vacuum pump 53 and the various rotation-inducing means 37, directing the abrasive stream 5 away from the longitudinal axis 9 of the hand tool 1, where the rotating abrasive stream 5 is created and used, and into the evacuating channel 21 via the spiral-shaped groove 75.

Figure 14:
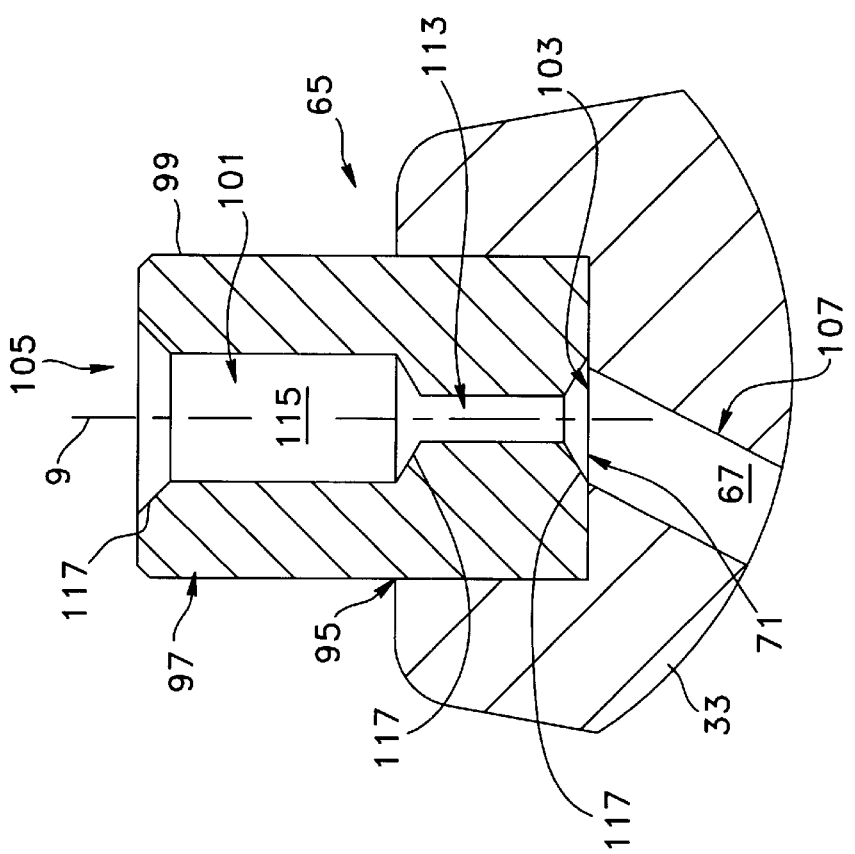
FIG. 14 is an enlarged plan view of the tip of the projection head shown in FIG. 12.

As better shown in FIG. 14, the projection channel 101 preferably has sections 113, 115 of different cross-sections so as to alter the velocity of the abrasive stream 6 projected through the projection nozzle 97. Preferably, an appropriate aspect ratio is selected between the different sections 113, 115 of different cross-section, as apparent to a person skilled in the art. Preferably also, tapered ends 117 are used to connect these different sections so as to allow for a smoother transition from one section 113, 115 to another.

As better shown in FIG. 2, the manipulative body 7 preferably further comprises a tubular channel 119 through which a fastening screw 121 is slidably inserted. Preferably, the tubular channel 119 extends within the manipulative body 7 along the longitudinal central axis 9 thereof and has first and second extremities 121, 123 located respectively at the first and second ends 11, 13 of the manipulative body 7. Preferably also, the fastening screw 125 has a first extremity 127 threadedly inserted into the projection head 33 through the base 63 thereof and a second extremity 129 in abutment with the second end 13 of the manipulative body 7, so that when the fastening screw 125 is threadedly inserted into the projection head 33 up to a certain point the projection head 33 becomes securely mounted onto the first end 11 of the manipulative body 7, with the first extremity 25 of the supply channel 17 being connected to the first extremity 69 of the feeding channel 67 and the first extremity 27 of the evacuating channel 21 being connected to the first extremity 77 of the spiral-shaped groove 75.

Figure 12:
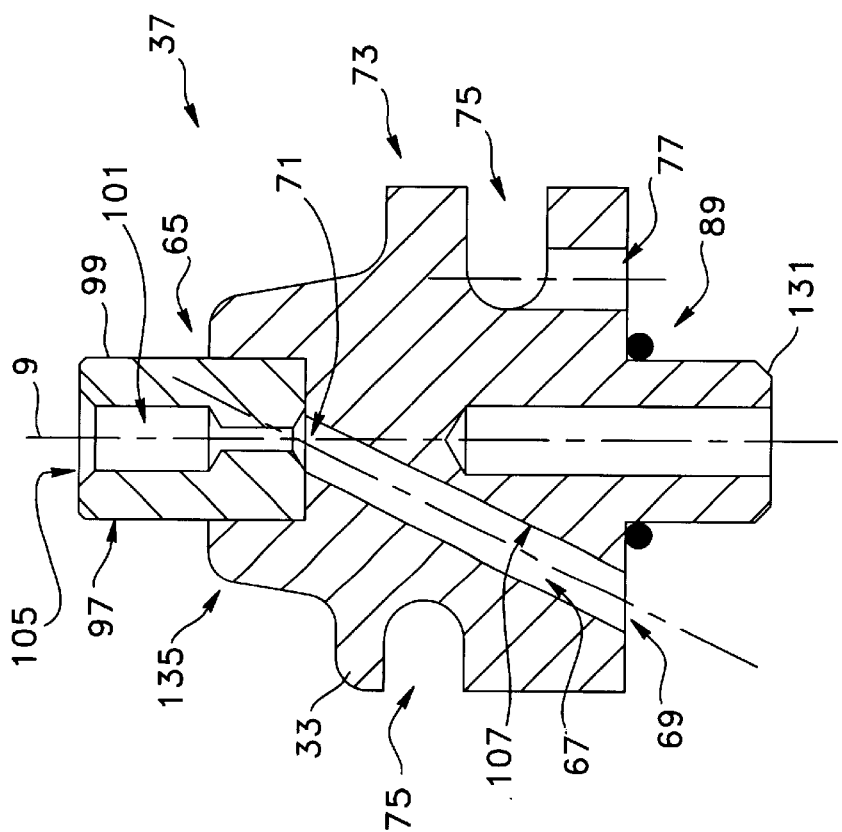
FIG. 12 is a cross-sectional view taken along section XII—XII of the projection head shown in FIG. 11

As better shown in FIGS. 12 and 13, the projection head 33 is preferably provided with a flange 131 protruding from the base 63 of the projection head 33 The flange 131 is preferably devised to be threadedly engaged with the first extremity 127 of the fastening screw 125 and is further devised to be inserted into a first alignment slot 133 provided at the first extremity 121 of the tubular channel 119 when the projection head 33 is securely mounted onto the manipulative body 7.

Preferably also and as better shown in FIGS. 7 to 10, the first end 11 of the manipulative body 7 is provided with a dowel pin 135 cooperating with a second alignment slot 137 on the base 63 of the projection head 33 when the projection head 33 is being mounted onto the manipulative body 7 so as to ensure that the first extremity 25 of the supply channel 17 is properly connected to the first extremity 69 of the feeding channel 67 and the first extremity 27 of the evacuating channel 21 is properly connected to the first extremity 77 of the spiral-shaped groove 75 when the projection head 33 is securely mounted onto the first end 11 of the manipulative body 7 by means of the fastening screw 125.

It is worth noting that different suitable mounting means, other than the above-described, may be used, as apparent to a person skilled in the art, for removably mounting the different components of the hand tool 1 together, such as the projection head 33 and manipulative body 7 for example, and for ensuring proper connection between the elements thereof, preferably in an air tight manner.

For example, FIGS. 18 to 21 illustrate a hand tool 1 according to another preferred embodiment of the invention. In this particular embodiment, the operative head 15 (and more particularly, the projection head 33) is removably fastened onto the manipulative body 7, as better shown in FIG. 20, and thus does not require a fastening screw 125. The illustrated modified base 63 of the projection head 33 is inserted and fastened into a cavity of the manipulative body 7, the cavity being defined by the first end 11 of the manipulative body 7 and a peripheral lip 138 thereof, as also better shown in FIG. 20. Hence, in light of the aforementioned, it should be easily understood that various modifications can be made to the hand tool 1 without departing from the scope of the invention, as apparent to a person skilled in the art.

Figure 7:
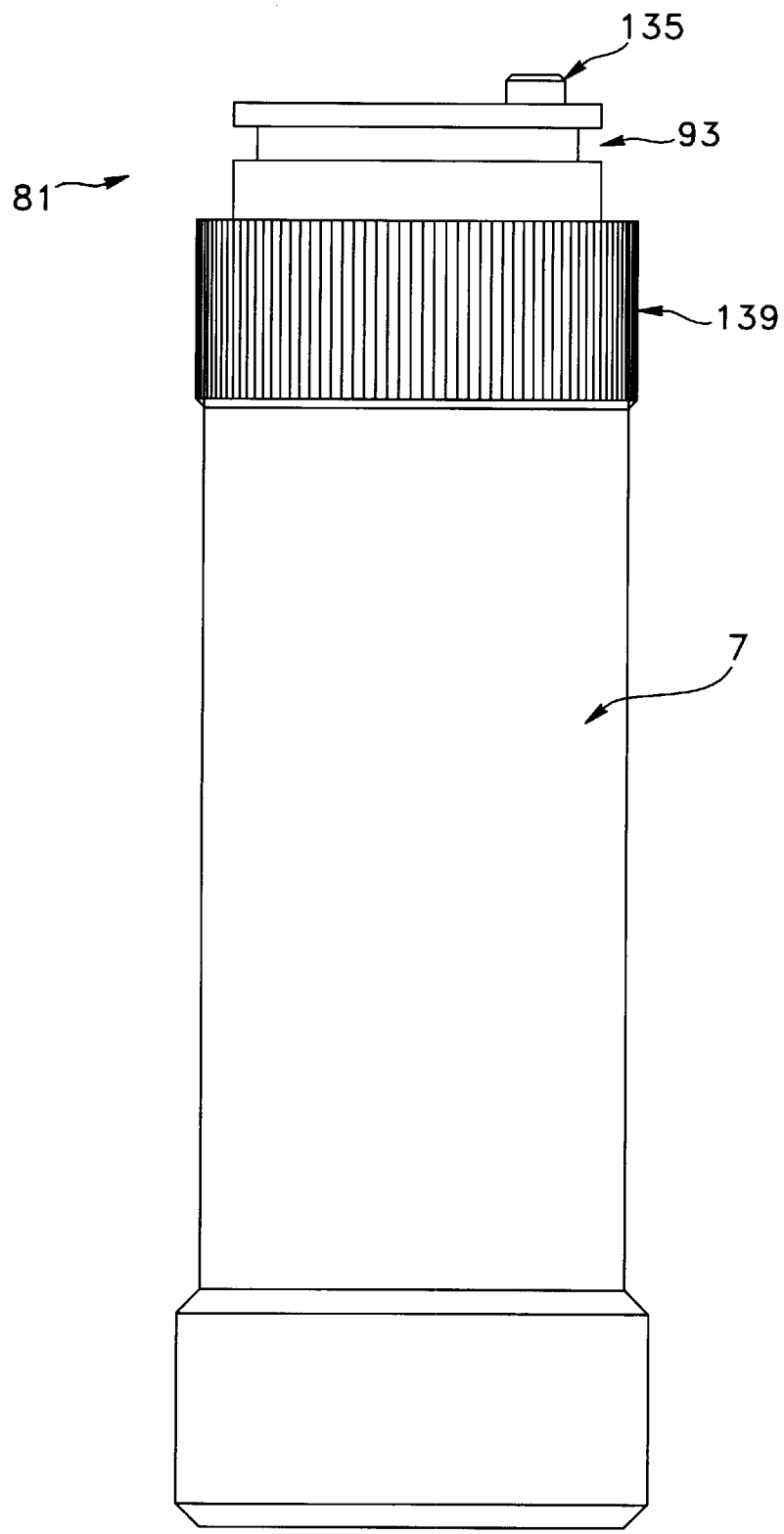
FIG. 7 is a plan view of the manipulative body of the hand tool shown in FIG. 1.
Figure 8:
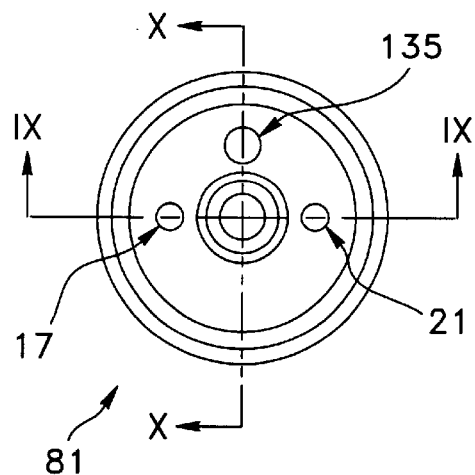
FIG. 8 is a top plan view of the manipulative body shown in FIG. 7.
Figure 9:
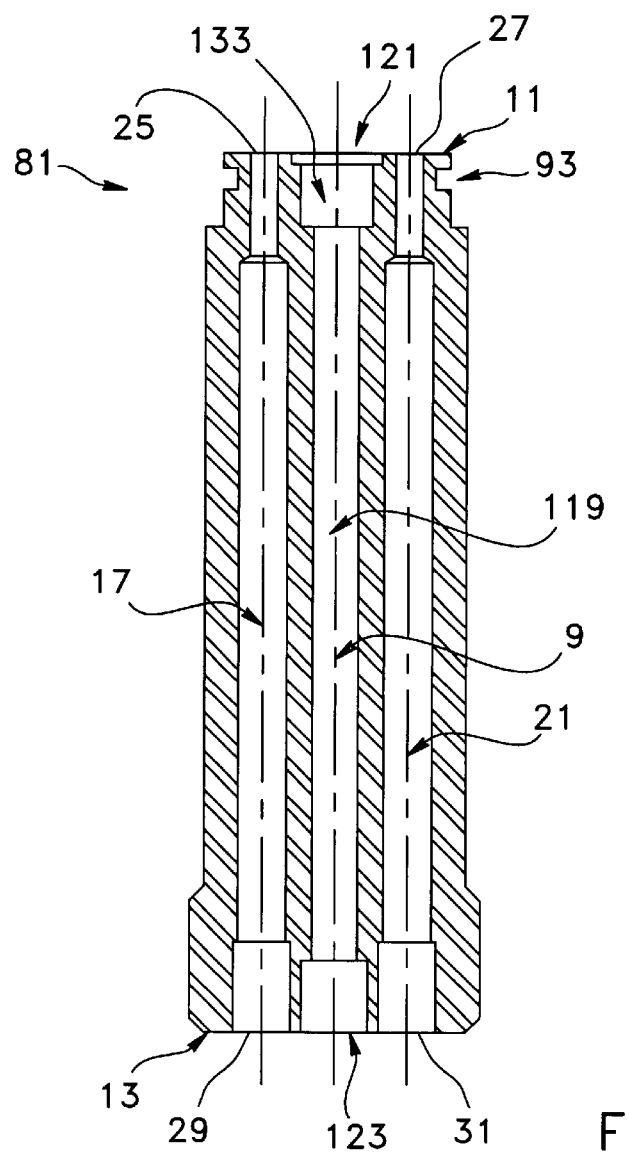
FIG. 9 is a cross-sectional view taken along section IX—IX of the manipulative body shown in FIG. 8.
Figure 10:
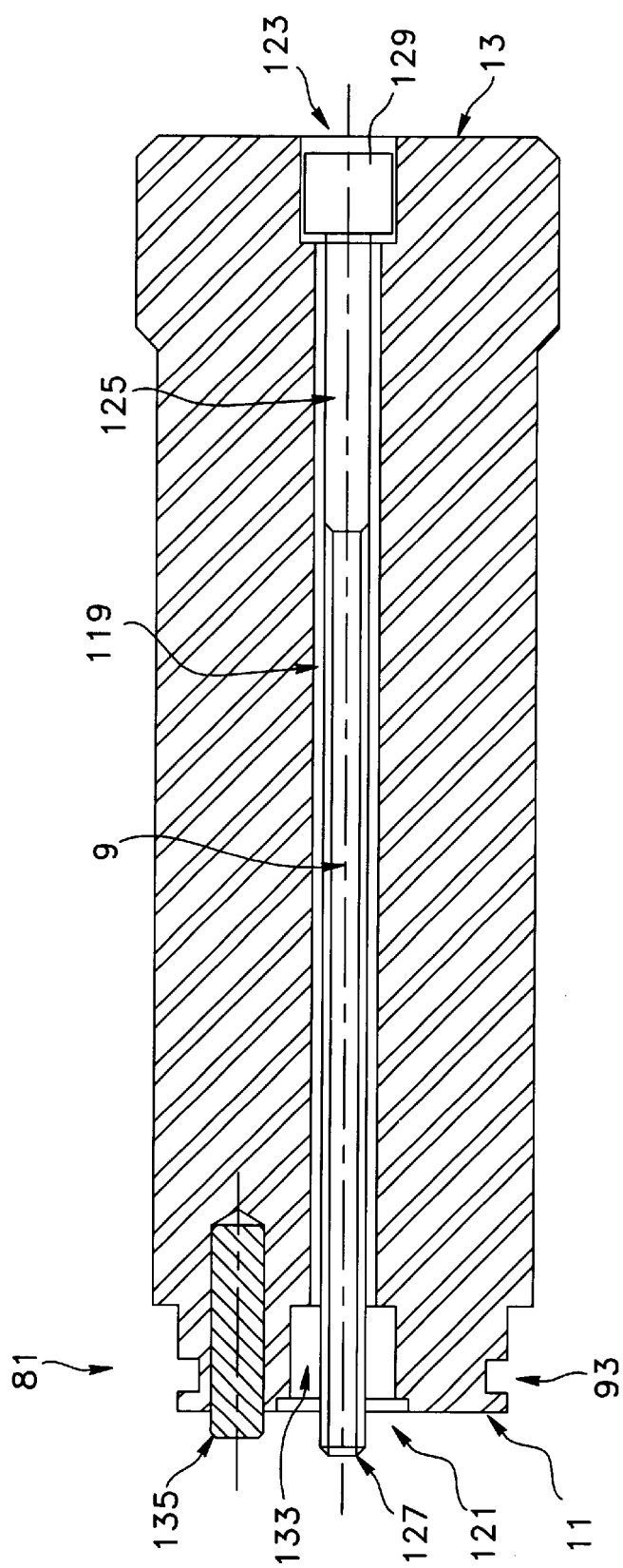
FIG. 10 is a cross-sectional view taken along section X—X of the manipulative body shown in FIG. 8.

As better shown in FIG. 7, the manipulative body 7 preferably has a substantially tubular shape and provides an ergonomic grip to the hand tool 1. Preferably also, the manipulative body has a knurled outer surface 139 for facilitating hand gripping of the hand tool 1.

As may now be appreciated, the present invention comprises several advantages and is thus a substantial improvement over the devices known in the art.

Firstly, the hand tool 1 according to the present invention enables a controlled and adjustable removal of superficial skin surface 3 by the projection of an abrasive stream 5 onto the skin surface 3 to be removed, as explained hereinabove. Indeed, the working principle of the hand tool 1 and of the different regulators 47, 49, 61 of the different components of the dermabrasion system 2 enable to provide a substantially homogeneous, stable, controlled, and adjustable removal of skin surface 3, in that a given velocity and pattern for the abrasive stream 5 may be selected by the operator of the present invention. For example, the removably interchangeable projection nozzles 97 enable to vary the parameters of the treatment carried out by the abrasive stream 5 being projected, depending on the particular needs of the treatment as required by the hand tool 1. Therefore, the present invention enables for a wide range of skin abrasions, ranging from a light abrasion where the outermost layers of the epidermis are removed, to a much deeper abrasion where the dermis is involved. This ability to provide a wide range of skin abrasion depths and patterns is very advantageous.

Another substantial improvement of the present invention, as also explained hereinabove, is that the hand tool 1 enables a substantially more even skin abrasion pattern than what is possible with the devices known in the prior art, both in surface geometry and in time. Indeed, the hand tool 1 is devised to be operated orthogonally with respect to the skin surface 3 being treated, thereby making operating and handling of the device much easier throughout the entire duration of the treatment than what is possible with some of the hand tools known in the art which are devised to be operated at a tilted angle with respect to the skin surface 3. Therefore, the present invention allows for a more uniform skin abrasion pattern throughout the duration of the treatment, and because the hand tool 1 is devised to be operated orthogonally to the skin surface 3 to be removed, the present invention also provides axisymmetrical abrasion patterns, and more particularly a circular abrasion pattern, similar to a circular "rubbing" effect, which is also very advantageous Moreover, the evacuating means 23 are designed to optimize the vacuum stability of the system 2 over extended periods of time.

The present invention is also an improvement over the prior art in that unlike the devices available in the trade, the present invention enables to project and retrieve the abrasive stream 5 to and from the skin surface 3 to be removed in a rotational pattern and orthogonally thereto. This important feature of the present invention enables an efficiently abraded skin surface 3 with a dimensionally very stable stream 5 of fine abrasive powder. The various rotation-inducing means 37 of the present invention, such as the turbine-like type projection nozzle 97 for example, induce rotation of the abrasive stream 5, as would the threaded internal surface of a "gun barrel". The combined use of these different rotation-inducing means 37 combined with the use of a geometrically orthogonal projection surface, enable all parts of the abrasive stream 5 to hit the skin surface 3 at a substantially same orthogonal angle and one must further take into consideration the fact that external portions of the stream 5 benefit from a transfer of the induced rotation, and hence, carry an "angle" component which is desirable when hitting the treated skin surface 3. Furthermore, the rotation induced in the evacuation chamber 35 of the hand tool 1 permits optimal tangential exhaust of the removed skin surface 3 and used abrasive stream 5 from the work area located near and on the longitudinal axis 9 of the hand tool 1.

Therefore, the operative head 15 can be schematically divided into three (3) operative zones. A first operative zone where the abrasive stream 5 being projected is rotationally induced by some of the independently active rotation-inducing means 37, such as the coaxial grooves 109, 107 provided in the projection nozzle 97 and feeding channel 67, as well as the slits 111 of the projection nozzle 97. A second operative zone where, after the abrasive stream 5 has been projected onto the skin surface 3 to be abraded, the used abrasive stream 5 and removed skin surface 3 are rotationally exhausted away from the longitudinal axis 9 by other independently active rotation-inducing means 37, such as the slits 111 and the coaxial grooves 110 which may be provided along the internal surface 112 of the cap 83. Finally, a third operative zone where the used abrasive stream 5 and the removed skin surface 3 are further whirpooled by other independently active rotation-inducing means 37, such as the grooves 110 of the cap 83 and the spiral-shaped groove 75, so as to be evacuated into the evacuating channel 21 via said spiral-shaped groove 75.

Hence, the various rotation-inducing means 37 of the present invention, as explained hereinabove, combine their effect to provide several distinct advantages to the whole system 2. Firstly, great stability of the projected abrasive stream 5 is achieved through particle rotation around the central axis of the abrasive stream 5. Furthermore, the rotation of the particles creates a homogeneous sweeping action in the manner of a generally rotational rubbing motion at the surface 3 of the skin. This second effect reduces the non-desirable "skin stabbing" effect common to the orthogonal surface powder projection systems known in the art. Moreover, desirable abrasive stream stability is further enhanced by the fact that a whirlpool ordered and generally peripheral unobstructed motion of powder particles exit the work zone tip area, as explained hereinabove. Such a centrifugal induced rotational geometry powder exit flow results in a highly desirable minimal collision occurrence with the incoming abrasive stream 5 projected from the projection head 33. As a result of the above-discussed, both the efficiency of the treatment of the skin surface 3 and the efficiency of the evacuation of the abrasive stream 5 are increased compared to the devices known in the prior art.

Finally, the present invention is also advantageous in that the hand tool 1 is easy to assemble, easy to use, and easy to maintain, as explained hereinabove. Indeed, most of the components of the present invention are removably mounted to one another, thereby making assembling, cleaning, replacement, etc. of the components very easy. Furthermore, the ergonomic design of the hand tool 1 also provides a more comfortable and easier handling and operating thereof.

Of course, numerous modifications could be made to the above-described embodiments without departing the scope of the invention as defined in the appended claims.

What is claimed is:

1. A dermabrasion hand tool for abrasively removing a skin surface by means of an abrasive stream projected onto the skin surface to be removed, the abrasive stream after projection onto said skin surface becoming a used abrasive stream, said hand tool comprising:

an elongated manipulative body having a longitudinal axis and first and second opposite ends;

an operative head through which the abrasive stream is projected onto the skin surface to be removed and through which the removed skin surface and used abrasive stream are evacuated, said operative head being removably mounted onto the first end of the manipulative body; and a supply channel for supplying the abrasive stream to the operative head from a supply stream source, and an evacuating channel for evacuating the removed skin surface and used abrasive stream from the operative head to an evacuating means, both of said channels extending within and along the manipulative body and each having first and second extremities located respectively at the first and second ends of the manipulative body;

wherein the operative head comprises:

a projection head for projecting the abrasive stream orthogonally to the skin surface to be removed, the projection head further comprising:

a base connected to the first end of the manipulative body;

a tip opposite to the base and through which the abrasive stream is projected;

a peripheral outer surface extending between the base and the tip; and a feeding channel extending inside the projection head from the base to the tip, the feeding channel having a first extremity in communication with the first extremity of the supply channel and a second extremity located adjacent to the tip of the projection head through which the abrasive stream is projected;

an evacuation chamber operatively connected to the evacuating channel for facilitating evacuation of the removed skin surface and used abrasive stream into said evacuating channel; and rotation-inducing, means for giving a rotational pattern to the abrasive stream projected from the operative head, the rotation-inducting means comprising:

a spiral-shaped groove extending coaxially about a portion of the peripheral outer surface of the projection head, said spiral-shaped groove having a first extremity in communication with the first extremity of the evacuating channel and a second extremity located on the peripheral outer surface of the projection head between the base and the tip, said spiral-shaped groove cooperating with the evacuation chamber to evacuate the removed skin surface and used abrasive stream from the evacuation chamber into the evacuating channel.

2. A dermabrasion hand tool according to claim 1, wherein the first end of the manipulative body comprises a rim onto which a cap is removably mounted, said cap encasing the projection head and forming said evacuating chamber around the projection head so as to facilitate evacuation of the removed skin surface and used abrasive stream via the spiral-shaped groove, said cap comprising a throughhole through which the abrasive stream is projected onto the skin surface to be removed and through which the removed skin surface and used abrasive stream are sucked back into the evacuation chamber so as to be evacuated via the spiral-shaped groove through the evacuating channel.

3. A dermabrasion hand tool according to claim 2, wherein the tip of the projection head comprises a slot projecting inwardly into the tip of the projection head, said slot being devised to allow a projection nozzle to be removably inserted into said tip so as to adjust the flow of the abrasive stream projected through the tip of the projection head.

4. A dermabrasion hand tool according to claim 3, wherein the projection nozzle consists of a hollow member comprising an outer surface and an inner cylindrical projection channel, said protection channel comprising a first extremity connected to the second extremity of the feeding channel and a second extremity through which the abrasive stream is projected.

5. A dermabrasion hand tool according to claim 1, wherein the rotation-inducing means comprise at least one coaxial groove provided along the feeding channel of the projection head so as to induce the rotational pattern onto the abrasive stream projected through said feeding channel.

6. A dermabrasion hand tool according to claim 2, wherein the rotation-inducing means comprise at least one coaxial groove provided along an internal surface of the cap so as to induce an additional rotational pattern to the removed skin surface and used abrasive stream being evacuated from the evacuation chamber into the evacuating channel via the spiral-shaped groove.

7. A dermabrasion hand tool according to claim 4, wherein the rotation-inducing means comprise at least one coaxial groove provided along the projection channel of the projection nozzle so as to induce the rotational pattern to the abrasive stream projected through said projection channel.

8. A dermabrasion hand tool according to claim 4, wherein the rotation-inducing means also comprise at least one lateral slit provided on the projection nozzle, said at least one slit extending from the projection channel to the outer surface of the projection nozzle and cooperating with the evacuation chamber so as to induce the rotational pattern to the abrasive stream projected through the projection nozzle.

9. A dermabrasion hand tool according to claim 4, wherein the projection channel has sections of different cross-sections so as to alter the velocity of the abrasive stream projected through the projection nozzle.

10. A dermabrasion hand tool according to claim 2, wherein the cap is made of a transparent material to allow a user of the hand tool to see the abrasive stream being projected and the removed skin surface and used abrasive stream being evacuated.

11. A dermabrasion hand tool according to claim 2, wherein the rim is provided with a gasket so as to provide a seal between the manipulative body and the cap mounted thereon.

12. A dermabrasion hand tool according to claim 1, wherein the manipulative body comprises a tubular channel through which a fastening screw is slidably inserted, said tubular channel extending within the manipulative body along the longitudinal axis thereof and having first and second extremities located respectively at the first and second ends of the manipulative body, said fastening screw having a first extremity threadedly inserted into the projection head through the base thereof and a second extremity in abutment with the second end of the manipulative body, so that when the fastening screw is threadedly inserted into the projection head up to a certain point, the projection head becomes securely mounted onto the first end of the manipulative body, with the first extremity of the supply channel being connected to the first extremity of the feeding channel and the first extremity of the evacuating channel being connected to the first extremity of the spiral-shaped groove.

13. A dermabrasion hand tool according to claim 12, wherein the projection head is provided with a flange protruding from the base of the projection head, said flange being devised to be threadedly engaged with the first extremity of the fastening screw and being further devised to be inserted into a first alignment slot provided at the first extremity of the tubular channel when the projection head is securely mounted onto the manipulative body.

14. A dermabrasion hand tool according to claim 13, wherein the first end of the manipulative body is provided with a dowel pin cooperating with a second alignment slot on the base of the projection head when the projection head is being mounted onto the manipulative body so as to ensure that the first extremity of the supply channel is connected to the first extremity of the feeding channel and the first extremity of the evacuating channel is connected to the first extremity of the spiral-shaped groove when the projection head is securely mounted onto the first end of the manipulative body by means of the fastening screw.

15. A dermabrasion hand toot according to claim 1, wherein the manipulative body has a knurled outer surface for facilitating hand gripping of the hand tool.

16. A dermabrasion hand tool according to claim 7, wherein the rotation-inducing means also comprise at least one lateral slit provided on the projection nozzle, said at least one slit extending from the projection channel to the outer surface of the projection nozzle and cooperating with the evacuation chamber so as to induce the rotational pattern to the abrasive stream projected through the projection nozzle;

the projection channel has sections of different cross-sections so as to alter the velocity of the abrasive stream projected through the projection nozzle;

the cap is made of a transparent material to allow a user of the hand tool to see the abrasive stream being projected and the removed skin surface and used abrasive stream being evacuated;

the rim is provided with a gasket so as to provide a seal between the manipulative body and the cap mounted thereon;

the manipulative body comprises a tubular channel through which a fastening screw is slidably inserted, said tubular channel extending within the manipulative body along the longitudinal axis thereof and having first and second extremities located respectively at the first and second ends of the manipulative body, said fastening screw having a first extremity threadedly inserted into the projection head through the base thereof and a second extremity in abutment with the second end of the manipulative body, so that when the fastening screw is threadedly inserted into the projection head up to a certain point, the projection head becomes securely mounted onto the first end of the manipulative body, with the first extremity of the supply channel being connected to the first extremity of the feeding channel and the first extremity of the evacuating channel being connected to the first extremity of the spiral-shaped groove;

the projection head is provided with a flange protruding from the base of the projection head, said flange being devised to be threadedly engaged with the first extremity of the fastening screw and being further devised to be inserted into a first alignment slot provided at the first extremity of the tubular channel when the projection head is securely mounted onto the manipulative body;

the first end of the manipulative body is provided with a dowel pin cooperating with a second alignment slot on the base of the projection head when the projection head is being mounted onto the manipulative body so as to ensure that the first extremity of the supply channel is connected to the first extremity of the feeding channel and the first extremity of the evacuating channel is connected to the first extremity of the spiral-shaped groove when the projection head is securely mounted onto the first end of the manipulative body by means of the fastening screw; and the manipulative body has a knurled outer surface for facilitating hand gripping of the hand tool.

* * * * *